(12) United States Patent
Costes et al.

(10) Patent No.: US 9,931,634 B2
(45) Date of Patent: Apr. 3, 2018

(54) HIGH THROUGHPUT DNA DAMAGE QUANTIFICATION OF HUMAN TISSUE WITH HOME-BASED COLLECTION DEVICE

(71) Applicants: The Regents of The University of California, Oakland, CA (US); Exogen Biotechnology, Inc., Berkeley, CA (US)

(72) Inventors: Sylvain V. Costes, Albany, CA (US); Jonathan Tang, San Francisco, CA (US); Steven M. Yannone, Concord, CA (US)

(73) Assignees: The Regents of the Univeristy of California, Oakland, CA (US); Exogen Biotechnology, Inc., Berkeley, CA (US)

( * ) Notice: Subject to any disclaimer, the term of this patent is extended or adjusted under 35 U.S.C. 154(b) by 25 days.

(21) Appl. No.: 14/634,266

(22) Filed: Feb. 27, 2015

(65) Prior Publication Data
US 2016/0025709 A1    Jan. 28, 2016

Related U.S. Application Data

(60) Provisional application No. 61/945,741, filed on Feb. 27, 2014, provisional application No. 62/107,184, filed on Jan. 23, 2015.

(51) Int. Cl.
*G01N 33/50* (2006.01)
*A61B 5/15* (2006.01)
(Continued)

(52) U.S. Cl.
CPC ...... *B01L 3/5082* (2013.01); *A61B 5/150022* (2013.01); *A61B 5/15105* (2013.01); *A61B 5/15142* (2013.01); *A61B 5/150305* (2013.01); *A61B 5/150343* (2013.01); *A61B 5/150755* (2013.01); *B01L 3/021* (2013.01); *A61B 5/150412* (2013.01); *A61B 5/150503* (2013.01);
(Continued)

(58) Field of Classification Search
None
See application file for complete search history.

(56) References Cited

U.S. PATENT DOCUMENTS 6,502,699 B1 *  1/2003  Watson ............... A61L 2/18
                                          206/570
7,787,681 B2    8/2010  Zhang et al.
(Continued)

FOREIGN PATENT DOCUMENTS

WO    WO 2013/187973 A1    12/2013
WO    WO 2014/041340 A1    3/2014

OTHER PUBLICATIONS

U.S. Office Action dated May 2, 2016 issued in U.S. Appl. No. 14/378,617 [P062US].
(Continued)

*Primary Examiner* — Jill Warden
*Assistant Examiner* — Julie Tavares
(74) *Attorney, Agent, or Firm* — Tom Hunter; Weaver Austin Villeneuve & Sampson LLP

(57) ABSTRACT

Kits, methods and systems for providing a service to provide a subject with information regarding the state of a subject's DNA damage. Collection, processing and analysis of samples are also described.

10 Claims, 8 Drawing Sheets

(51) Int. Cl.
B01L 3/00 (2006.01)
A61B 5/151 (2006.01)
B01L 3/02 (2006.01)
(52) U.S. Cl.
CPC . B01L 2200/185 (2013.01); B01L 2400/0481 (2013.01)

(56) References Cited

U.S. PATENT DOCUMENTS

| | | | |
|---|---|---|---|
| 2003/0002627 A1 | 1/2003 | Espinosa et al. | |
| 2005/0232813 A1* | 10/2005 | Karmali | A61B 10/0096 422/410 |
| 2005/0255502 A1 | 11/2005 | D'andrea | |
| 2007/0099292 A1 | 5/2007 | Miller et al. | |
| 2007/0178044 A1 | 8/2007 | Halazonetis et al. | |
| 2009/0155838 A1* | 6/2009 | Hale | A61J 1/2093 435/29 |
| 2011/0312514 A1 | 12/2011 | D'andrea | |
| 2014/0171829 A1* | 6/2014 | Holmes | A61B 5/150305 600/575 |
| 2014/0227687 A1* | 8/2014 | Horlitz | C12Q 1/6806 435/6.1 |
| 2015/0017092 A1* | 1/2015 | Costes | G01N 21/253 424/1.11 |

OTHER PUBLICATIONS

U.S. Office Action dated Apr. 10, 2017 issued in U.S. Appl. No. 14/378,617 [P062US].
PCT International Search Report and Written Opinion dated Nov. 8, 2013 issued in PCT/US13/31727 [P062WO].
PCT International Preliminary Report on Patentability dated Sep. 16, 2014 issued in PCT/US13/31727 [P062WO].
Anderson, et al. (2007) "Effect of linear energy transfer (LET) on the complexity of alpha-particle-induced chromosome aberrations in human CD34+ cells." *Radiat Res* 167:541-550.
Anderson, et al. (2002) "M-FISH analysis shows that complex chromosome aberrations induced by alpha-particle tracks are cumulative products of localized rearrangements." *Proc Natl Acad Sci USA* 99:12167-12172.
Asaithamby, et al.(Apr. 28, 2009) "Cellular responses to DNA double-strand breaks after low-dose gamma-irradiation." *Nucleic Acids Res* 37(12):3912-3923.
Aten, et al. (Jan. 2, 2004) "Dynamics of DNA double-strand breaks revealed by clustering of damaged chromosome domains." *Science* 303:92-95.
Bakkenist, et al. (Jan. 30, 2003) "DNA damage activates ATM through intermolecular autophosphorylation and dimer dissociation." *Nature* 421:499-506.
Baure, et al. (2009) "Histone H2AX phosphorylation in response to changes in chromatin structure induced by altered osmolarity." *Mutagenesis* 24(2):161-167.
Bocker, et al. (Jan. 2006) "Computational Methods for analysis of foci: validation for radiation-induced gamma-H2AX foci in human cells." *Radial Res*, 165(1): 113-24.
Brenner, et al. (2006) "Estimating radiation-induced cancer risks at very low doses: Rationale for using a linear no-threshold approach." *Radiat Environ Biophys* 44:253-256.
Chatterjee, et al. (1973) "Radial cutoff LET and radial cutoff dose calculations for heavy charged particles in water." *Radiat Res* 54:479-494.
Chiolo, et al. (Mar. 4, 2011) "Double-strand breaks in heterochromatin move outside of a dynamic HP1a domain to complete recombinational repair." *Cell* 144:732-744.
Costes, et al. (2001) "Large-mutation spectra induced at hemizygous loci by low-LET radiation: Evidence for intrachromosomal proximity effects." *Radiat Res*, 156:545-557.
Costes, et al. (2000) "Quantitative image analysis of laminin immunoreactivity in skin basement membrane irradiated with 1 GeV/nucleon iron particles." *Radiat Res* 154 :389-397.
Costes, et al. (2006) "Imaging features that discriminate between foci induced by high and low-LET radiation in human fibroblasts." *Radiat Res*, 165:505-515.
Costes, et al. (2010) "Spatiotemporal characterization of ionizing radiation induced DNA damage foci and their relation to chromatin organization." *Mutat Res* 704:78-87. [NIH Public Access—Author Manuscript—19 pages].
Costes, et al. (Aug. 2007) "Image-based modeling reveals dynamic redistribution of DNA damage into nuclear sub-domains." *PLoS Comput Biol* 3(8): e155(1477-1488).
Du G, et al. (2011) "Spatial dynamics of DNA damage response protein foci along the ion trajectory of high-LET particles." *Radiat Res*, 176:706-715.
Hauptner A, et al. (2006) "DNA-repair protein distribution along the tracks of energetic ions." *Radiat Prot Dosimetry* 122(1-4):147-149.
Hickson, et al. (2004) "Identification and characterization of a novel and specific inhibitor of the ataxia-telangiectasia mutated kinase ATM." *Cancer Res* 64:9152-9159.
Jakob, et al. (2009) "Positional stability of damaged chromatin domains along radiation tracks in mammalian cells." *Radiat Res* 171:405-418.
Jakob, et al. (2011) "DNA double-strand breaks in heterochromatin elicit fast repair protein recruitment, histone H2AX phosphorylation and relocation to euchromatin." *Nucleic Acids Res* 39:6489-6499[11 Pages—doi:10.1093/nar/gkr230].
Jakob, et al. (Mar. 3, 2009) "Live cell microscopy analysis of radiation-induced Dna double-strand break motion." *Proc Natl Acad Sci USA* 106(9):3172-3177.
Karlsson, et al. (2008) "Repair of radiation-induced heat-labile sites is independent of DNA-PKcs, XRCC1 and PARP." *Radiat Res* 169:506-512.
Kato Ta, et al. (2008) "Comparison of the induction and disappearance of DNA double strand breaks and gamma-H2AX foci after irradiation of chromosomes in G1-phase or in condensed metaphase cells." *Mutat Res* 639:108-112.
Leatherbarrow, et al. (2006) "Induction and quantification of gamma-H2AX foci following low and high LET-irradiation." *Int J Radiat Biol* 82(2):111-118.
Lisby, et al. (Jun. 2003) "Colocalization of multiple DNA doublestrand breaks at a single Rad52 repair centre." with supplementary information, *Nat Cell Biol* 5(6):572-577 [16 pages].
MacPhail, et al. (2003) "Expression of phosphorylated histone H2AX in cultured cell lines following exposure to X-rays." *Int J Radiat Biol* 79(5):351-358.
Magee, et al. (1980) "Radiation chemistry of heavy-particle tracks. 1. General considerations." *J Phys Chem* 84:3529-3536.
Neumaier, et al. (2011) "Evidence for formation of DNA repair centers and dose-response nonlinearity in human cells." *PNAS Early Edition* www.pnas.org/cgi/doi/10.1073/pnas.1117849108 pp. 1-6.
Nikjoo, et al. (2001) "Computational approach for determining the spectrum of DNA damage induced by ionizing radiation." *Radiat Res* 156:577-583.
Nikjoo, et al. (1997) "Computational modelling of low-energy electron-induced DNA damage by early physical and chemical events." *Int J Radiat Biol* 71(5):467-483.
Olivo-Marin (2002) "Extraction of spots in biological images using multiscale products." *Pattern Recognition* 35:1989-1996.
Ponomarev, et al. (2008) "Stochastic properties of radiationinduced DSB: DSB distributions in large scale chromatin loops, the HPRT gene and within the visible volumes of DNA repair foci." *Int J Radiat Biol* 84:916-929.
Pope, et al. (Sep. 2011) "A portable microfluidic fluorescence spectrometer device for gamm-H2AX-based biological dosimetry." *Radiation Measurements*, 46(9): 907-911.
Rogakou, et al. (1998) "DNA double-stranded breaks induce histone H2AX phosphorylation on serine 139." *J Biol Chem* 273(10):5858-5868.

(56) References Cited

OTHER PUBLICATIONS

Rothkamm, et al. (Apr. 29, 2003) "Evidence for a lack of DNA double-strand break repair in human cells exposed to very low X-ray doses." *Proc Natl Acad Sci USA* 100(9):5057-5062.

Sachs, et al. (1999) "Locations of radiationproduced DNA double strand breaks along chromosomes: A stochastic cluster process formalism." *Math Biosci* 159:165-187.

Sachs, et al. (1997) "Review: Proximity effects in the production of chromosome aberrations by ionizing radiation." *Int J Radiat Biol* 71:1-19.

Savage (1996) "Insight into sites." *Mutat Res* 366:81-95.

Savage (2002) "Reflections and meditations upon complex chromosomal exchanges." *Mutat Res* 512:93-109.

Sethu, et al. (Aug. 1, 2006) "Microfluidic Isolation of Leukocytes from Whole Blood for Phenotype and Gene Expression Analysis." *Anal. Chem.* 78(15):5453-5461.

Stenerlow, et al. (2003) "Measurement of prompt DNA double-strand breaks in mammalian cells without including heat-labile sites: Results for cells deficient in nonhomologous end joining." *Radial Res* 159:502-510.

Tobias, et al. (1971) "Radiological physics characteristics of the extracted heavy ion beams of the bevatron." *Science* 174:1131-1134.

Wang, et al. (2001) "Efficient rejoining of radiation-induced DNA double-strand breaks in vertebrate cells deficient in genes of the RAD52 epistasis group." *Oncogene* 20:2212-2224.

Wilson, et al. (2010) "Inter-individual variation in DNA double-strand break repair in human fibroblasts before and after exposure to low doses of ionizing radiation." *Mutat Res* 683:91-97.

\* cited by examiner

HIGH THROUGHPUT DNA DAMAGE QUANTIFICATION OF HUMAN TISSUE WITH HOME-BASED COLLECTION DEVICE

CROSS-REFERENCE TO RELATED APPLICATIONS

This application claims benefit of and priority to U.S. Ser. No. 61/945,741, filed on Feb. 27, 2014 and to U.S. Ser. No. 62/107,184, filed on Jan. 23, 2015, both of which are incorporated herein by reference in their entirety for all purposes.

STATEMENT OF GOVERNMENTAL SUPPORT

This invention was made with government support under Contract No. DE-AC02-05CH11231 awarded by the U.S. Department of Energy. The government has certain rights in the invention.

BACKGROUND

Damage to the integrity of a cell's DNA may occur through a variety of mechanisms. For example, DNA breakage may be caused through chemical reaction as a result of ingestion or absorption of a drug or other chemical agent that reacts with DNA (see, e.g., Exon (2007) *J. Toxicol. Environ. Health B Crit. Rev.* 9(5), 397-412). DNA damage may also be induced by via physical means, such as exposure to ionizing radiation (see, e.g., Brendler-Schwaab et al. (2004) *Mutat. Res.,* 566(1): 65-91), either alone, or in combination with a chemical agent, e.g., by a photochemical mechanism.

Numerous studies suggest that certain human diseases create increase background level of oxidative DNA damage during their pathogenesis. These include, but are not limited to Alzheimer's disease (see, e.g., Mecocci et al. (1994) *Ann. Neurolog.* 36: 747-651; Prashad et al. (1996) *Proc. Natl. Acad. Sci. USA,* 93: 5146-5150), amyotrophic lateral sclerosis, Parkinson's disease, cataract formation, aging process, radiation exposure (see, e.g., Wilson et al. (1992) *Cancer Res.* 48: 2156-2162), ischemic damage and stroke (1996, NIH Guide 25), metal toxicity (see, e.g., Carmichael et al. (1995) *Mutat. Res.* 326: 235-243), breast cancer (Djuric et al. (1996) *Cancer,* 77: 691-696), carcinogenesis in general (see, e.g., Ames et al. (1995) *Proc. Natl. Acad. Sci. USA,* 92: 5258-5265). Molecular mechanisms, including the pathogenesis of oxidative DNA damage and alteration of a cell's ability to repair damaged DNA, may lead to the development of genomic instability. Genomic instability is believed to occur in an early step in the process of carcinogenesis. In addition, cells and human tissues are being screened for specific DNA damage in order to correlate the action of DNA damaging agents with human diseases and to verify the contribution of DNA damaging agents in specific genetic states to manifestation of human diseases.

Despite the utility of DNA damage analysis to determine risk for and/or prognosis of various pathologies, there are currently no systems in place for people to be able to take their blood at home and send it to a lab for DNA damage analysis. It is believed the closest to this is the RABiT (Rapid Automated Blodosimetry Tool, see, e.g., Garry et al. (2010) *Health Phys.* 98(2): 209-217) which is a completely automated, ultra-high throughput robotically-based biodosimetry workstation developed at Columbia University (see, e.g. cmcr.columbia.edu/rabit). RABiT uses advanced, high-speed automated image analysis and robotics to examine tissue samples (e.g., a fingerstick of blood) quickly for quantitative indicators of radiation exposure (e.g., fragments of DNA; DNA repair complexes). However, the RABiT system requires patients to be on site next to the machine and the assay is focused on radiation effects, has neglected sorting specific white cells and does not take into account the age of the person being analyzed. Knowledge and correction for these factors is in fact required for accurate interpretation of DNA damage levels. Moreover, these technologies may permit the detection of radiation hypersensitivities in humans prior to exposure to medical x-rays, such a practical capability does not currently exist.

SUMMARY

In one embodiment, we describe a kit and a method that permits the in-home collection of small blood samples and the immediate fixation of biological activity in blood cells. The fixation conditions are such that the blood can be shipped and/or stored without changes in the signal of interest (DNA-break marker proteins).

In another embodiment, a rapid and efficient means to isolate such 'fixed' leukocytes for immunofluorescent analysis. The presently described systems and methods provide for distinct variations from general laboratory protocols that facilitate the entire process of in-home blood collection, shipping, cell isolation and immunofluorescent analyses. The present set of procedures allows for application of established laboratory technologies to end users remote from the laboratory without the need for cell culture or laboratory visits by individuals.

In one embodiment, the methods comprise a blood collection and fixation protocol to reliably quantify DNA damage from a small volume of blood, like that typically obtained via finger-prick (e.g., ~10-100 ul).

In some embodiments, a process to fix and collect nucleated lymphocytes in a manner that left them amenable to immunostaining. This would allow for the reproducible quantification of DNA damage levels in a human sample from a small volume of blood (e.g., one or a few drops, e.g., about 10 µl to 200 µl, or about 20 µl to about 100 µL, or about 30 µl to about 70 µl, and in certain embodiments, about ~50 µl).

In certain embodiments, the process provides for measurement and analysis of the DNA damage levels in the human sample.

In various embodiments, the DNA damage levels are compared to a baseline or other reference level. In some embodiments, the reference level is determined by the average number of breaks/cell in a population taking into account factors such as age, health status, presence or absence of disease, background, location, exposure to toxins, or health or physical factor. In some embodiments, the subject is provided the results of the comparison.

In certain embodiments, data from the same individual collected over time allows optimization of DNA damage levels using corrective lifestyle changes or nutritional regimen.

In certain embodiments, quantitative DNA damage data is provided to the subject and in some embodiments, a corrective lifestyle change or regimen is advocated or prescribed by a health professional based on the diagnosis information provided.

In various aspects, the invention(s) contemplated herein may include, but need not be limited to, any one or more of the following embodiments:

Embodiment 1

A home collection kit including a sterile blood-drawing device (e.g., a lancet device or other needle devices, including but not limited to vacuum blood-drawing tubes], a capillary blood collection device coated with an anti-coagulant to avoid coagulation, patient blood collection tubes containing a fixative and anti-coagulant, wherein the fixative provides fixation conditions such that the blood can be shipped and/or stored without substantial changes in the signal of interest (DNA-break markers).

Embodiment 2

The kit of embodiment 1, wherein said capillary blood collection device is configured to collect about 10 µl to about 200 µl, or about 10 µl to about 100 µl of blood.

Embodiment 3

The kit of embodiment 1, wherein said capillary blood collection device is configured to collect about 50 µl of blood.

Embodiment 4

The kit according to any one of embodiments 1-3, wherein said anticoagulant includes EDTA or heparin.

Embodiment 5

The kit according to any one of embodiments 1-3, wherein said anticoagulant includes EDTA.

Embodiment 6

The kit of kit according to any one of embodiments 1-5, wherein said anticoagulant is selected from the group consisting of paraformaldehyde, methanol, ethanol, acetone, and urea.

Embodiment 7

The kit of embodiment 6, wherein said fixative includes paraformaldehyde.

Embodiment 8

The kit of kit according to any one of embodiments 1-7, wherein said fixative includes: an anticoagulant; paraformaldehyde; and a buffer.

Embodiment 9

The kit of embodiment 8, wherein said anticoagulant includes about 10 mM up to about 100 mM EDTA.

Embodiment 10

The kit according to any one of embodiments 8-9, wherein said buffer includes phosphate buffered saline at about pH 7 to about pH 8.

Embodiment 11

The kit according to any one of embodiments 8-10, wherein said buffer includes phosphate buffered saline at pH about 7.4.

Embodiment 12

The kit according to any one of embodiments 8-11, wherein said fixative includes about 0.1 percent up to about 10% paraformaldehyde.

Embodiment 13

The kit according to any one of embodiments 8-11, wherein said fixative, when mixed with blood leads to a mix of fixative and blood with a final concentration of 1% paraformaldehyde and 25 mM EDTA.

Embodiment 14

The kit of embodiment 13, wherein the fixative includes about 2% paraformaldehyde and 50 mM EDTA in PBS, and the volume of fixative provided in the collection tube is such that fixative and whole blood are mixed in a 1:1 ratio when the capillary collection device is dispensed into the fixative containing sample container.

Embodiment 15

The kit according to any one of embodiments 1-14, wherein said sterile blood-drawing lancet device is a finger-pricking lancet.

Embodiment 16

The kit according to any one of embodiments 1-14, wherein said sterile blood-drawing lancet device is a heel-pricking lancet.

Embodiment 17

The kit according to any one of embodiments 1-16, wherein said lancet device is a disposable lancet.

Embodiment 18

The kit according to any one of embodiments 1-17, wherein said lancet is a disposable one-use lancet.

Embodiment 19

The kit according to any one of embodiments 1-18, wherein said kit includes a sample (collection) tube holder.

Embodiment 20

The kit according to any one of embodiments 1-19, wherein said kit includes a capillary tube holder.

Embodiment 21

The kit according to any one of embodiments 19-20, wherein said sample tube holder and/or said capillary tube holder is formed from the kit container.

Embodiment 22

The kit according to any one of embodiments 1-21, wherein said kit further includes a disinfectant swab and/or a drying pad, and/or a dressing.

Embodiment 23

The kit according to any one of embodiments 1-22, wherein said kit contains a plurality of packets, each packet containing a finger-pricking lancet.

Embodiment 24

The kit of embodiment 23, wherein each packet further contains includes a disinfectant swab and/or a drying pad, and/or a dressing.

Embodiment 25

The kit according to any one of embodiments 1-24, wherein said kit includes a storage container for holding patient blood collection tubes during storage and/or shipping.

Embodiment 26

The kit according to any one of embodiments 1-25, wherein said kit includes instructional materials teaching the use of the kit components for collecting a blood sample.

Embodiment 27

The kit of embodiment 26, wherein said instructional materials comprise written materials.

Embodiment 28

The kit according to any one of embodiments 26-27, wherein said instructional materials comprise a DVD containing a video illustrating use of the kit.

Embodiment 29

The kit according to any one of embodiments 1-28, wherein said kit further includes a shipping container.

Embodiment 30

The kit of embodiment 29, wherein said shipping container includes a shipping envelope.

Embodiment 31

A method for the in-home collection of small blood samples and the immediate fixation of biological activity in blood cells, said method including: collecting a blood sample using a kit according to any one of embodiments 1-30 to deposit one or more blood samples in sample collection tube(s).

Embodiment 32

A method for reliably quantifying DNA damage from a small volume of blood, like that typically obtained via finger-prick (~10-100 μl), said method including: receiving one or a plurality of collection (sample) tubes containing a blood sample collected utilizing a kit according to any one of embodiments 1-30; and processing said sample to determine the amount of DNA damage.

Embodiment 33

The method of embodiment 32, wherein said processing said sample, comprise a method selected from the group consisting of PCR, comet assay, halo assay, terminal deoxyribonucleotidyl transferase-mediated deoxyuridine triphosphate nick end labeling (TUNEL) assay, HPLC-electrospray tandem mass spectrometry, fluorescence in situ hybridization (FISH), flow cytometry, electrochemical detection assay, and immunofluorescent staining.

Embodiment 34

The method according to any one of embodiments 32-33, wherein said processing includes isolating lymphocytes from said blood sample.

Embodiment 35

The method according to any one of embodiments 32-34, wherein said method includes immunofluorescent staining of molecular markers for DNA double-strand breaks.

Embodiment 36

The method of embodiment 35, wherein said immunofluorescent staining includes staining for one or more markers selected from the group consisting of P53 binding protein 1 (53BP1), γH2AX, Rad51, MRE11, NBSI, XRCC1, hOGG1, Rad50, BRCA1, BRCA2, ATM, ATR, DNApkcs MLH1, 5mC, and 5hmC.

Embodiment 37

The method of embodiment 36, wherein said immunofluorescent staining includes staining for γH2AX.

Embodiment 38

The method according to any one of embodiments 32-37, wherein said method includes quantifying the number and/or frequency of DNA double strand breaks.

Embodiment 39

A method of fixing and collecting nucleated lymphocytes in a manner that leaves said lymphocytes amenable to immunostaining, said method including: pricking a body surface to produce a drop of blood; collecting said blood in a capillary collection device including an anticoagulant; and delivering the blood from the capillary collection device into a sample holder containing a fixative where said fixative provides fixation conditions such that the blood can be shipped and/or stored without substantial changes in the signal of interest (e.g., DNA-break markers).

Embodiment 40

The method of embodiment 39, wherein said method is practice using a kit according to any one of embodiments 1-30.

Embodiment 41

A process for automatic computer scoring and analysis of the DNA damage levels in the human sample.

Embodiment 42

A method for providing a service to provide a subject information regarding the state of a subject's DNA damage, said method comprising:

a) receiving one or more sample containers from a home collection kit according to any one of embodiments 1-30 from a subject where said container(s) containing the subject's blood sample are and fixed in the collection tubes;
b) isolating T, B and/or NK cells from said blood sample by
  i. conducting hypotonic lysis of erythrocytes (red blood cells) in fixed blood samples;
  ii. capturing of T, B, and/or NK cells from said sample using CD-specific antibodies;
  iii. coupling the antibody captured fixed T, B and/or NK cells to magnetic beads or nanoparticles;
  iv. exposing the antibody captured fixed T, B and/or NK cells coupled to magnetic beads or nanoparticles tubes to a strong magnetic field to immobilize the cells; and
  v. washing away unwanted cells and serum components leaving target cells of interest;
c) affixing the isolated cells to the surface by an adhesive;
d) labeling affixed cells with primary antibodies recognizing DNA damage markers and with secondary antibodies that are covalently conjugated to fluorescent chromophores to provide labeled cells; and
e) imaging said labeled cells and scoring for DNA breaks in the cells.

Embodiment 43

The method of embodiment 42, wherein said antibodies that recognize DNA damage markers comprise one or more antibodies selected from the group consisting of anti-P53 binding protein 1 (anti-53BP1), anti-γH2AX, anti-Rad51, anti-MRE11, anti-NBS1, anti-XRCC1, anti-hOGG1, anti-Rad50, anti-BRCA1, anti-BRCA2, anti-ATM, anti-ATR, anti-DNApkcs anti-MLH1, anti-5mC, and anti-5hmC.

Embodiment 44

The method according to any one of embodiments 42-44, further including comparing the DNA damage levels to a baseline or other reference level.

Embodiment 45

The method of embodiment 44, wherein the reference level is determined by the average number of breaks in a population taking into account factors of age, health status, presence or absence of disease, background, location, exposure to toxins, or health or physical factor.

Embodiment 46

The method according to any one of embodiments 42-45, further including providing the subject the results of step e and/or the comparison in embodiments 44-45.

Embodiment 47

The method according to any one of embodiments 42-46, further including providing a diagnosis to the subject and prescribing a corrective lifestyle change or regimen or based on the diagnosis provided.

Embodiment 48

The method according to any one of embodiments 42-47, wherein steps b (iv) and (v) are repeated with successive washes and chemical processing of cells in suspension without losing cells.

Embodiment 49

A method for providing a service to provide a subject with information regarding the state of a subject's DNA damage, said method comprising:
a) receiving one or more sample containers from a home collection kit according to any one of embodiments 1-30 from a subject containing a subject's blood sample collected and fixed in the collection tubes;
b) isolating and/or identifying specific cell types for DNA damage scoring of cell type-specific DNA damage measurements from said blood sample by:
  i. conducting a cell type in fixed blood samples;
  ii. capturing of said cells from said sample using cell type-specific antibodies;
  iii. coupling the antibody captured cells to magnetic beads or nanoparticles;
  iv. exposing the antibody captured fixed cells coupled to magnetic beads or nanoparticles tubes to a strong magnetic field to immobilize the cells; and
  v. washing away unwanted cells and serum components leaving target cells of interest;
c) affixing the isolated cells to the surface by an adhesive;
d) labeling affixed cells with primary antibodies recognizing DNA damage markers and with secondary antibodies that are covalently conjugated to fluorescent chromophores; and
e) imaging said labeled cells and score for DNA breaks in the cells.

Embodiment 50

The method of embodiment 49, further including comparing the DNA damage levels to a baseline or other reference level.

Embodiment 51

The method of embodiment 50, wherein the reference level is determined by the average number of breaks in a population taking into account factors of age, health status, presence or absence of disease, background, location, exposure to toxins, or health or physical factor.

Embodiment 52

The method of embodiment 49, further including step f providing the subject the results of step e and/or the comparison in embodiment 50.

Embodiment 53

The method of embodiment 49, further including providing a diagnosis to the subject and prescribing a corrective lifestyle change or regimen or based on the diagnosis provided.

Definitions.

The term "subject" and "patient" are used interchangeably to refer to a mammal from which a biological sample is obtained to determine sensitivity to ionizing and/or non-ionizing radiation. Subjects can include humans and non-human mammals (e.g., a non-human primate, canine, equine, feline, porcine, bovine, lagomorph, and the like).

BRIEF DESCRIPTION OF THE DRAWINGS

FIG. 2A illustrates a sterile finger-pricking lancet device, a sterile/disinfecting swab, a drying pad, and a dressing. FIG. 2B illustrates packaging (e.g. a box) that form a capillary tube holder and/or a sample tube holder. Also shown is a sample canister containing sample tubes. FIG. 2C illustrates placement of the capillary tube in the capillary tube holder and sample tube in the sample tube holder. FIGS. 2D to 2K illustrate use of a finger prick lancet (FIG. 2D), formation of a blood drop (FIG. 2E), transfer of the drop to the capillary blood collection device (FIG. 2F and FIG. 2G), transfer of the blood from the capillary blood collection device into the sample tube (FIG. 2H), placement of the labeled sample tube(s) into the canister (FIGS. 2I and 2J), and closure of the sample canister (FIG. 2K).

DETAILED DESCRIPTION

Figure 1A:
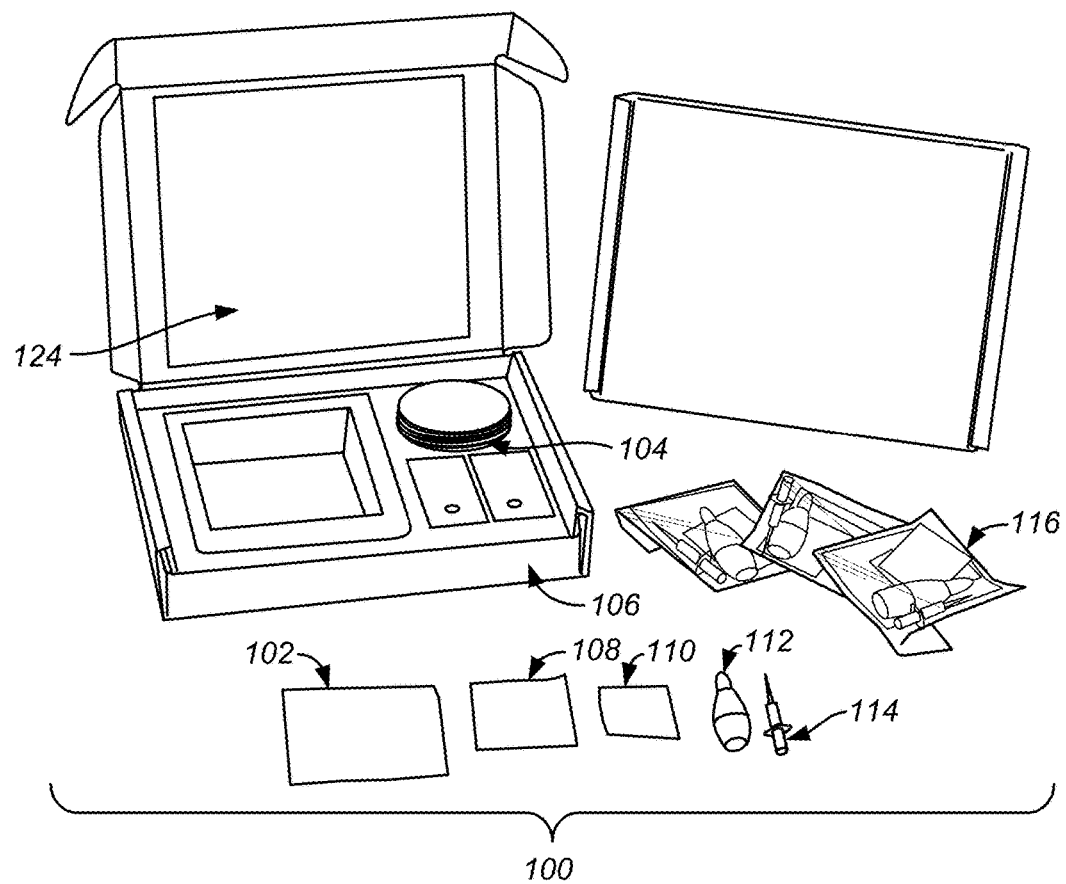
FIG. 1A shows one illustrative, but non-limiting embodiment of a home collection kit for the collection of blood samples for DNA damage evaluation. As illustrated the kit can include a sterile finger-pricking lancet device, a capillary blood collection device, a sample canister, a sterile swab, a drying pad, and a dressing (e.g. bandage). The kit typically also contains blood collection tubes (sample tubes) that, in certain embodiments, are stored in the sample canister. The components can be provided in packaging (e.g., a box) that can also provide a sample tube holder and/or a capillary tube holder and can be used to provide instructional materials as illustrated. Certain components of the kit can be grouped together in packages.

In various embodiments methods and devices (e.g., kits) for rapidly collecting, and stabilizing a blood sample, in a manner that permits accurate assessments of DNA damage, e.g., at a later time and different location. The methods and devices permit the rapid and efficient determination of DNA damage and/or sensitivity to radiation or other agents that damage DNA, and/or the effect that various agents and factors (e.g., lifestyle factors) have on reduction or other alteration in DNA damage. Such measurements have numerous uses.

For example, in certain embodiments, such measurements can be used in radiotherapy. Using such an assay, permits prediction/identification of subjects that are likely to have an acute reaction to repeated exposures of high levels of ionizing (or non-ionizing) radiation. In case of a predicted sensitivity, a modified therapy could be proposed and administered to the patient. For example, one could reduce the total dose per session and increase the numbers of sessions (e.g., hyperfractionated radiotherapy), and/or one could increase the recovery period between sessions, and/or one could distribute the entrance paths (e.g., for external radiation sources) to improve skin sparing.

In medical imaging if a subject is determined to be sensitive to ionizing radiation, the information would allow a patient, and/or a doctor, and/or an insurance plan to justify the usage of medical devices or therapy that do not involve ionizing radiation (e.g. MRI, ultrasound, chemotherapy, etc.).

The methods and devices described herein also find use in monitoring subjects occupationally exposed to radiation, various chemicals, or other possible causes of DNA damage. Employers could constrain sensitive employees to a lower annual radiation or chemical exposure limit. For example, the maximum limit of ionizing radiation is 1000 mrem/year for regular employees at LBNL. However pregnant women are considered sensitive employees with an annual limit of 500 mrem.

The methods and devices described herein can also be used to identify at risk subjects in a population subject to possible environmental exposure from a radiation source (e.g., in the instance of a nuclear plant failure or material release), or chemical source (e.g., chemicals leaching into ground water), etc.

Similarly the methods and devices described herein can provide subjects the ability to evaluate the effect of lifestyle changes (e.g., diet, exercise, nutritional supplements, etc.) on DNA damage.

In various embodiments kits are provided herein that provide subjects the ability to obtain a biological sample at home in a manner that provides a stable sample that can be shipped to a laboratory for accurate assessment of DNA damage. Notably the kits described herein, facilitate the collection of a very small amount of blood (e.g., blood (e.g., one or a few drops, e.g., about 10 μl to 200 μl, or about 20 μl to about 100 μL, or about 30 μl to about 70 μl, and in certain embodiments, about ~50 μl, or about 25 μl), which is then rapidly fixed, stored, and shipped in a manner that permits accurate assessments of DNA damage, e.g., at a later time and/or different location.

The methods, systems, and kits described herein result, in part from the convergence of two fields, radiation biology and treatment of immunological disorders. The inventors have worked extensively in the study of radiation effects on human cells and more specifically the damage caused to DNA after exposure to ionizing radiation. In particular, the effects of low-dose exposures to human cells, and the biochemical pathways and genetic defects that impact both the repair of radiation-induced DNA damage and immunogenesis have been extensively studied. The primary goal of these basic studies was to understand the potential impacts of radiation and DNA repair functions on cancer risk, immunological function and treatments, and most generally on human health. Out of these broad areas of research came an understanding of the present methods and systems to score the amount of DNA damage present in an individual at any given time using a simple collection kit.

Illustrative Embodiments

In certain embodiments, the kits described herein permit the development and use of a service to provide a subject with information regarding the state of a subject's DNA damage.

For example, in one embodiment, kits and methods are provided that permit the in-home collection of small blood samples and the immediate fixation of biological activity in blood cells so that DNA damage in those cells is stabilized and can provide a reliable measure of DNA damage in the subject from whom the sample is drawn. The fixation conditions are such that the blood can be shipped and/or stored without changes in the signal of interest (e.g., DNA-break markers such as proteins, genes, chromosomes, other cellular markers). Blood and DNA collection kits and procedures are described in more detail herein.

Rapid and efficient means to isolate 'fixed' leukocytes for immunofluorescent analysis are described herein. Measurement of a subject's DNA damage in peripheral blood cells (e.g., B cells, T cells, NK cells, and circulating tumor and stem cells) is carried out and such analysis may be provided to the subject. In some embodiments, the amount of DNA damage sustained by a subject can be measured and correlated to a subject's calculated risk that is associated with diseases or outcomes such as cancer, or other age-related diseases. In some embodiments, the amount of DNA damage present in a subject can be quantified and correlated to an individual's radiation dose received during accidental or medical exposure.

Kits:

In certain embodiments the in-home collection kit uses alcohol swabs to sterilize and disinfect the site of collection, lancets to puncture the skin, and capillaries to collect and measure the blood volume. The kit can, optionally, contain instructions describing how to collect one blood sample, or multiple blood samples, e.g., over a period of days into collection tube(s) provided in the kit. In some embodiments, the kit further comprises a return envelope and instructions regarding shipping to the provider for analysis.

Fixatives:

Typically the kits include a fixation solution, e.g., a mix of chemicals in aqueous solution designed to:
1) Immediately halt biological activity in living cells;
2) Disrupt and halt enzymatic activities within the sample, (i.e. kinase activity and phosphatase activity);
3) Preserve the blood cell structures and DNA damage markers in a manner amenable to shipping through commercial carriers (e.g., FedEx),
4) To be non-toxic and to comply with shipping regulations; and
5) To be compatible with downstream cell isolation and immunofluorescent staining procedures.

In an illustrative, but non-limiting embodiment, this fixation solution may contain up to about 10 mM up to about 100 mM, preferably about 50 mM EDTA, 1-10% paraformaldehyde and a buffer (e.g., phosphate buffered saline, e.g., about pH 7 to about pH 8, typically about pH 7.4) among other components. In certain embodiments, other fixatives such as methanol, ethanol, acetone, urea, and the like may be used.

As noted above, in various embodiments, the kits can contain means to package, store, and ship collected samples in a manner that essentially preserves the original amount of DNA damage so that it can be later ascertained (e.g., at a remote laboratory).

Once the sample is received by the processing facility (e.g., a clinical or specialty laboratory) the amount of DNA damage is ascertained. Numerous methods are known for assessing/quantifying DNA damage.

PCR is one of the most reliably used techniques for detecting DNA damage as the amplification stops at the site of the damage. Numerous PCR-based methods are known. For example, TDPCR (Terminal transferase dependent PCR) has been used for the mapping of pyrimidine (6-4) pyrimidone photoproducts (64PP) (see, e.g., Rochette et al. (2006) *Photochem. Photobiol.*, 82: 1370-1376). Other PCR approaches include, but are not limited to RAPD (random amplified polymorphic DNA) and rDNA amplification (see, e.g., Kumar et al. (2004) *Biochem. Biophys. Res. Comm.* 318: 1025-1030, immuno-coupled PCR (ICPCR) (see, e.g., Karakoula et al. (2003) *J. Immunol. Meth.* 277: 27-37) which estimates T< >T (thymine dimer), PCR-based SINE (short interspersed DNA element)-47 mediated detection (see, e.g., Wang et al. (1999) *Mutat. Res.* 433: 147-157) which utilizes the abundance, dispersion and conservation of SINEs, and the like.

The comet assay (single-cell gel electrophoresis) was first described by Olive et al. (1990). As the name indicates, it is the detection of DNA damage in individual cell and estimation of its distribution in cell population. This technique is used to detect mainly single-strand breaks, double-strand breaks, oxidative DNA damage, and single-strand breaks associated with incomplete excision repair sites (see, e.g., Olive (1998) *Radiat. Res.* 150: S42-S51; Olive et al. (1993) *Int. J. Radiat. Biol.* 64: 349-358; Olive and Banath (1995) *Radiat. Res.* 142: 144-152; Olive et al. (1990) *Radiat. Res.* 122: 86-94; Olive et al. (1991) *Cancer Res.* 51: 4671-4676; Olive et al. (1992) *Exp. Cell Res.* 198: 259-267; Vijayalaxmi et al. (1992) *Mutat. Res.* 271: 243-252, and the like). Comet may be combined with the FLARE™ (Fragment Length Analysis using Repair Enzymes) assay which detects DNA damage in single cells using a variety of DNA repair enzymes. The extent of the DNA damage can be assessed qualitatively or quantitatively using image analysis software to calculate tail length and tail moment.

The halo assay (Vinograd et al. (1965) *Proc. Natl. Acad. Sci. USA*, 53: 1104-1111; Roti Roti and Wright (1987) *Cytometry* 8: 461-467) uses propidium iodide (PI), a fluorescent dye that intercalates into the DNA helix and causes the change in supercoiling status of the DNA. Thus, DNA can be seen as a fluorescent halo that changes diameter with PI concentration and can provide a measure of chromatin fragility and alterations of DNA organization.

The terminal deoxyribonucleotidyl transferase-mediated deoxyuridine triphosphate nick end labeling (TUNEL) assay detects DNA fragmentation by fluoresceinating the free ends of the DNA. Consequently, with the use of fluorescence microscopy one can detect single and double strand DNA breaks (see, e.g., Bruggeman et al. (1997) *J. Clin. Invest.* 100: 84-92; Gavrieli et al. (1992) *J. Cell Biol.* 119: 493-501; McGahon et al. (1994) *Blood,* 83: 1179-1187; Migheli et al. (1995) *J. Pathol.* 176: 27-35; and the like).

In HPLC-electrospray tandem mass spectrometry the soft ionization property of electrospray allows to assess the DNA adducts with bulky chemicals (see, e.g., Wolf and Vouros (1994) *Chem. Res. Toxicol.* 7: 82-88.; Rindgen et al. (1995) *Chem. Res. Toxicol.* 8: 1005-1013) and UV-induced dimeric pyrimidine photoproducts. It also allows the detection of cis-syn and trans-syn I cyclobutane thymine dimers (c-s T< >T and t-s T<>T, respectively) (see, e.g., Douki et al. (2000) *J. Biol. Chem.* 275: 11678-11685).

In certain embodiments fluorescence in situ hybridization (FISH) can be used to determine copy number and/or relative location of disturbed cellular DNA content in nuclei or chromosome (see, e.g., Murthy and Demetrick (2006) *Meth. Mol. Biol.* 319: 237-259.).

Flow cytometry can be used to detecting chromosomal aberrations, sister-chromatid exchange, chemical adducts to DNA and DNA strand breakage (see, e.g., Lower and Kandall in In McCarthy J F, Shugart L R (eds). *Biomarkers of environmental contamination* (pp 309-31), Boca Raton: Lewis Publ., 1990; Shugart, In McCarthy J F, Shugart L R (eds). Biomarkers of environmental contamination (pp 205-16). Boca Raton, Fla.: Lewis Publ. 1990; Deaven In Hsu T C (ed.) *Cytogenetic assays of environmental mutagens* (pp 325-351) Totowa: Allanheld, Osmun and Co. Publ., 1982; Bickham In Sandhu S S, Lower W R, de Serres F J, Suk W A, Tice R R (eds.) *In situ evaluation of biological hazards*

*of environmental pollutants* (pp 97-108), New York: Plenum Pr., 1990; Bickham et al. (1994) *Cytometry,* 15: 222-229; and the like). Additionally, nucleotide excision repair has been also detected by alkaline unwinding FCM assay (Thyagarajan et al. (2007) *Mutagenesis,* 22: 147-153).

Electrochemical methods offer a sensitive, selective approach for the detection of DNA damage (see, e.g., Paleček et al. (1998) *Biosens. Bioelectron.* 13: 621-628; Lee and Shim (2001) *Anal. Chem.* 73: 5629-5632; Darain et al. (2004) *Biosens. Bioelectron.* 20: 857-863); Rahman et al. (2005) *Anal. Chem.* 77: 4854-4860; Cahová-Kuchaříková et al. (2005) *Anal. Chem.* 77: 2920-2927). DNA is an electroactive and surface-active substance yielding analytically valuable electrochemical signals. Adenine, cytosine, and guanine undergo redox processes at the mercury electrodes while guanine and adenine are oxidizable at carbon and some other solid electrodes. Some of these signals respond to the changes in DNA structure (Paleček et al. In Bard A J, Stratsmann M (eds.) *The encyclopedia of electrochemistry*, Vol. 9: Bioelectrochemistry (pp 365-429). Weinheim: Wiley-VCH, 2002; Fojta (2002) *Electroanalysis,* 14: 1449-1463; Fojta (2004) *Collect Czech Chem. Commun.* 69: 715-747). 8-oxoguanine has been detected via its oxidation signal at carbon electrodes (Langmaier et al. (2003) *Electroanalysis,* 15: 1555-1560; Brett et al. (2000) *Electroanalysis,* 12: 969-973). Lesions such as thymine dimers can be electrochemically detected when they are associated with distortions of DNA double helix (Fojta (2002) *Electroanalysis,* 14: 1449-1463; Fojta (2004) *Collect Czech Chem. Commun.* 69: 715-747).

These approaches are illustrative and non-limiting. Another approach includes, but is not limited to, cell isolation and immunofluorescent staining and it was discovered that presently claimed methods are particularly well suited to immunofluorescent detection of markers of DNA damage in isolated leukocytes.

Cell Isolation:

One illustrative method of cell isolation exploits immunoaffinity of the "cluster of differentiation" (CD) cell surface markers. Using commercially available isolation kits and antibodies sold for live cell isolation, a protocol was developed to isolate various intact leukocyte lineages from whole blood. Unlike standard protocols, the isolations occur after fixation on metabolically inactive intact cells. In certain embodiments the isolation protocol can include hypotonic lysis of erythrocytes (red blood cells) followed by potential immunoaffinity capture of T cells, B cells, NK cells, circulating tumor cells, and/or stem cells using CD-specific antibodies. The antibody (e.g., IgG)-coupled cells can then be bound to magnetic beads or nanoparticles. The tubes containing the IgG coupled cells coupled to the magnetic beads are placed into a strong magnetic field. The target cells are immobilized and unwanted cells and serum components are washed away leaving target cells of interest. In various embodiments modifications to commercial protocols include, reduced blood volumes, which are typically milliliter volumes, and can be reduced to microliter volumes in the assays herein. Additionally, we have established protocols for the isolation of fixed cells while commercial protocols are typically designed and sold for the isolation of live cells.

Additional Cell Isolation Approaches:

In some cases it may be useful to isolate multiple lymphocyte lineages. This can be achieved by isolation of fixed cells by density gradient centrifugation using 10-20% ficoll and collecting the lymphocyte layer. This method produces a mix of peripheral blood mononuclear cells (PBMCs) including most CD45+ cells but primarily T, B, NK, granulocytes, and monocytes. This technology is routinely used for live cell isolations from milliliter volumes of whole blood, but can be adapted to isolate fixed cells from small volumes of blood (e.g., typically 20-50 microliters).

Likewise, to isolate mixed populations of leukocytes, the small-volume magnetic nanoparticle protocol described above can be applied for isolation of CD45+ cells or any other desired CD-discriminated cell type from whole fixed blood samples collected from a finger prick.

Immunofluorescent Staining:

In certain embodiments, to score DNA damage in the isolated cells, molecular markers for DNA double-strand breaks are visualized using immunofluorescent techniques. Illustrative markers include, but are not limited to P53 binding protein 1 (53BP1), γH2AX, Rad51, MRE11, NBSI, XRCC1, hOGG1, Rad50, BRCA1, BRCA2, ATM, ATR, DNApkcs MLH1, 5mC, and 5hmC. Labeled antibodies (e.g., fluorescently labeled antibodies) directed against these marketers are commercially available.

In one illustrative, but non-limiting embodiment, isolated blood cells are affixed to the plastic surface at the bottom of wells in a multi-well plate (e.g., in a 96-well plate). This is facilitated by a cellular adhesive designed for this purpose (e.g., BD Cell Tak or other commercially available product). Wells are coated with adhesive and rinsed according to manufacturer's instructions. In some embodiments, cellular adhesion is obtained by coating plates with antibody binding to specific leukocytes cell surface markers such as CD45. This can be facilitated by protein A-G pre-coating. The isolated fixed lymphocytes suspended in buffer (e.g., PBS) are added to the wells and allowed to settle and adhere to the plates at 4° C. for 10-24 hours, or centrifuged at 20×g for 10 min at 4° C., or driven to the plate surface using a magnetic field. The attached cells are then treated with Methanol or Triton X-100 or other permeabilization treatment and, the cells washed with PBS and bovine serum albumin to block non-specific antibody adhesion. The blocked cells are then incubated with antibodies recognizing DNA damage markers (e.g., 53BP1, γH2AX, XRCC1, hOGG1, MLH1, 5mC, and 5hmC, among others) for sufficient time to permit antibody binding (e.g., 15 minutes to 4 hours, in certain embodiments about 1 hour) at 37° C. The primary antibodies are removed and the cells washed 3× with PBS/BSA and then incubated with secondary antibodies that are covalently conjugated to fluorescent chromophores. The secondary antibodies are removed, the cells washed and anti-fade solution is added. Plates are transported to the automated imaging microscope and scored for DNA breaks/cell and/or DNA breaks/cell/cell type.

Illustrative Kit and Method of Use.

Figure 1B:
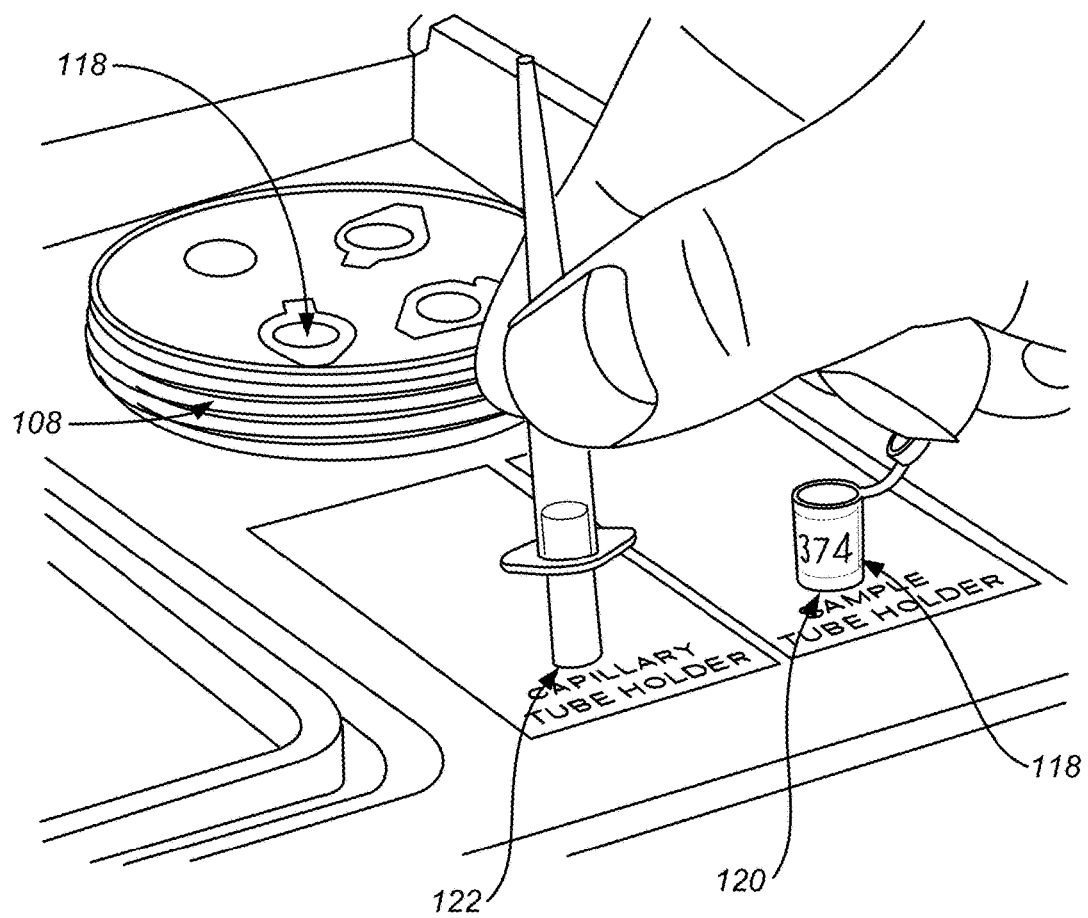
FIG. 1B shows a portion of the kit comprising a storage canister, capillary tube holder, and sample tube holder. The sample tube and capillary tube are illustrated as well.

FIG. 1A shows one illustrative, but non-limiting embodiment of a home collection kit for the collection of blood samples for DNA damage evaluation. As illustrated in FIG. 1A, kit 100 includes a sterile finger-pricking lancet device 112, a capillary blood collection device 114 that may be coated with EDTA and/or other agents to prevent blood clotting, and patient blood collection tubes (sample tubes) 118 (see FIG. 1B) containing a fixative and, optionally an anti-coagulant. In certain embodiments the blood collection tubes 118 are labeled with an alphanumeric label and/or a bar code or other computer readable code label to provide a sample ID. The blood collection tubes 118 are stored in a sample canister 104 and are not visible in FIG. 1A. The sample canister 104 can provide support and protection of the sample tubes, particularly during shipping. In certain embodiments, the capillary collection device can further comprise an expulsion means (e.g., a plunger, wick, or other device) to transfer collected blood into a sample tube 118. In certain embodiments, as illustrated in FIG. 1B, the kit can further comprise a sample tube holder 120 and/or a capillary tube holder 122. In certain embodiments the sample tube holder and/or capillary tube holder can be fabricated from the kit packaging 106 as illustrated in FIGS. 1A and 1B or can be provided as a separate structure.

In certain embodiments the kit can optionally further include a sterile swab 108 (e.g., an alcohol swab) for cleaning the pin-prick site, and/or a drying pad 102 (e.g., a gauze pad) for drying the site, and/or a dressing 110 (e.g. bandage) for dressing the site after pin prick.

In certain embodiments, the components for a single collection operation are packaged together in a packet 116. Such packets can include, for example, a single use disposable finger pricking lancet device 112, a capillary blood collection device 114, a sterile swab 108, a drying pad 102, and a dressing 110. In certain embodiments the sample tubes are stored separately (e.g., in a sample canister) or can be included in each packet 116. In certain embodiments the kit includes at least 2 packets, or at least 3 packets, or at least 4 packets, or at least 5 packets, or at least 6 packets, or at least 7 packets, or at least 8 packets. In certain embodiments, the kit contains 1, 2, 3, 4, 5, 6, 7, 8, 9, 10, 11, 12, 13, 14, 15, or 16 packets.

The kit can further contain instructional materials 124 teaching collection methods utilizing the kit components and, optionally, providing guidance to overcome problems that may occur during collection. Often and typically the instructional materials are provided in written form and can be printed on the kit components themselves (e.g. on the cover of a box, container, or on an envelope, or can be provided as an insert/instructional page or booklet. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Figure 2A:
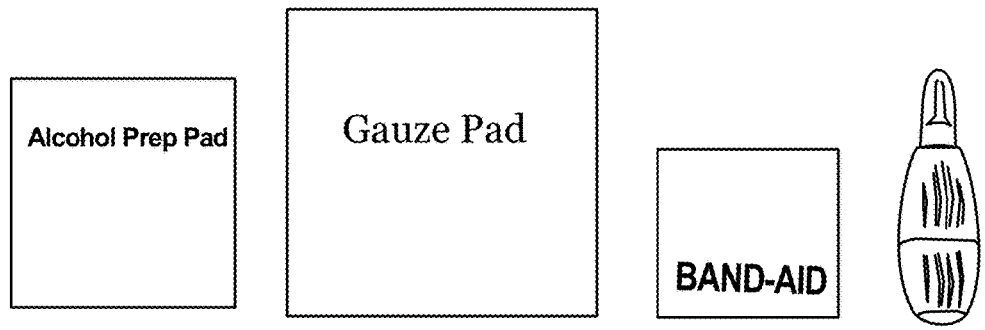
FIGS. 2A-2K show components of an illustrative, but non-limiting embodiment of a home collection kit for the collection of blood samples for DNA damage evaluation and the use of that kit.
Figure 2B:
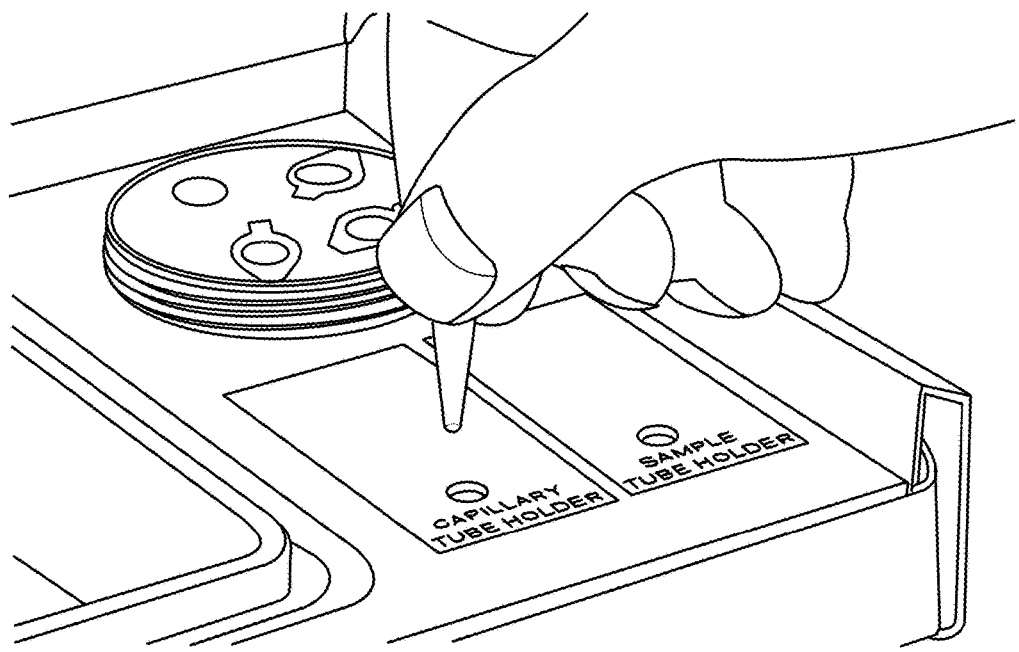
Figure 2C:
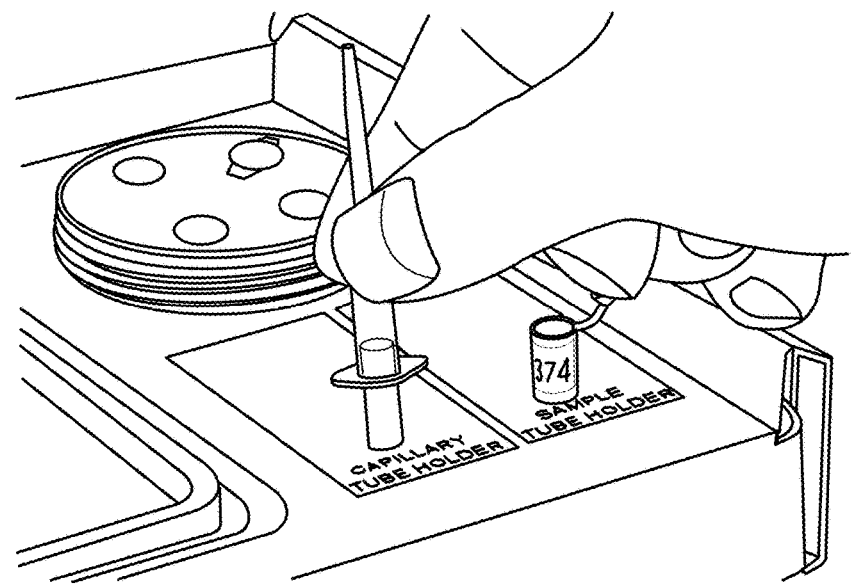
Figure 2D:
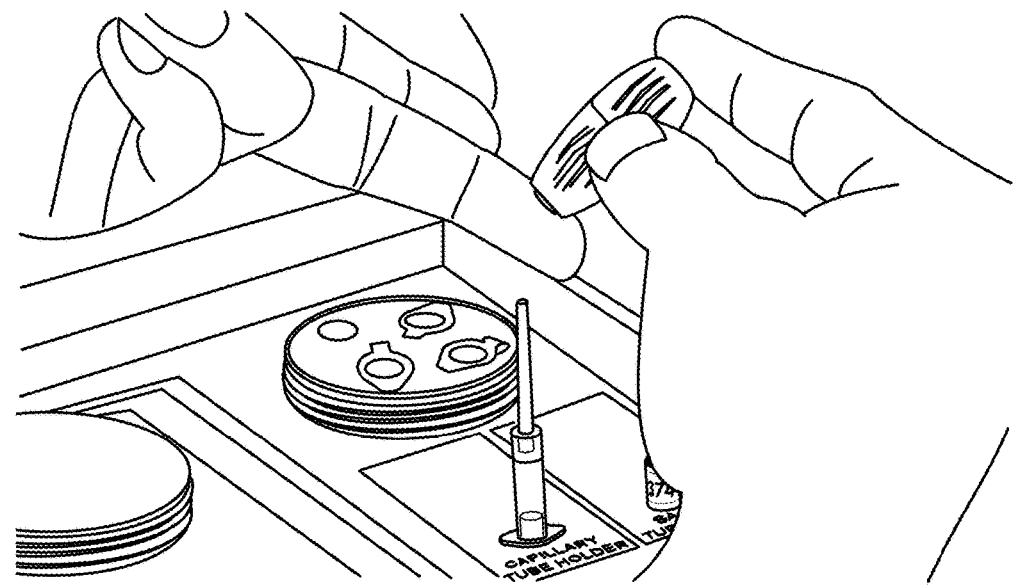
Figure 2E:
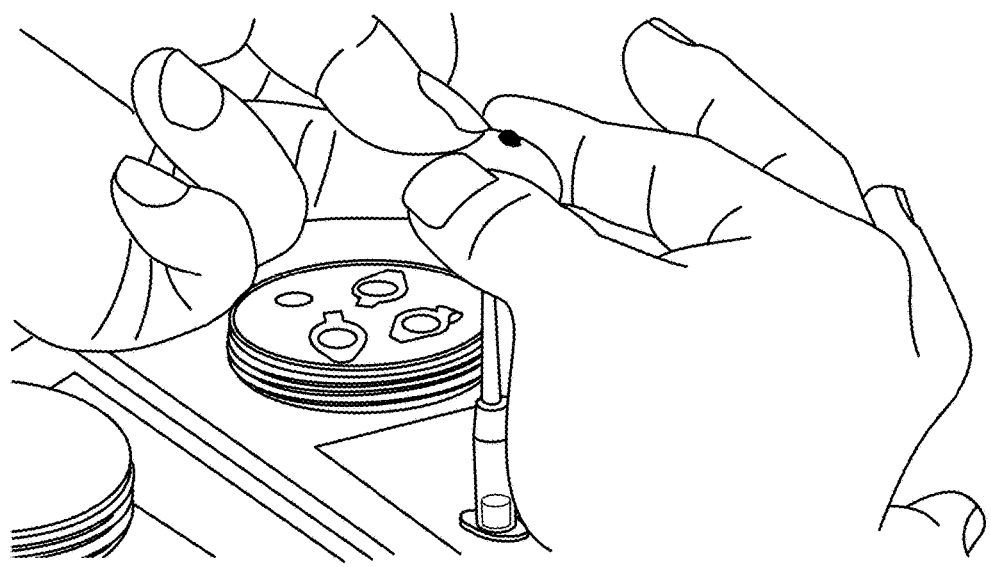
Figure 2F:
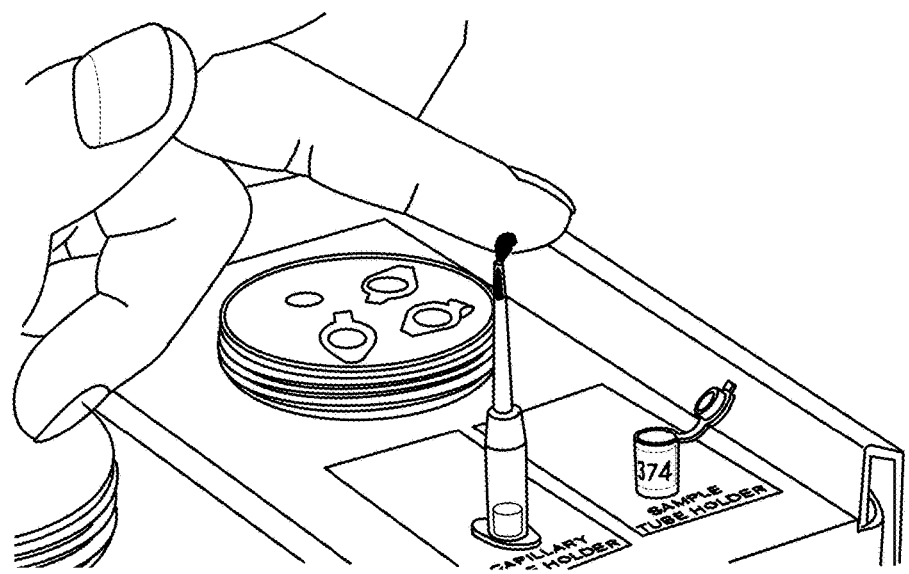
Figure 2G:
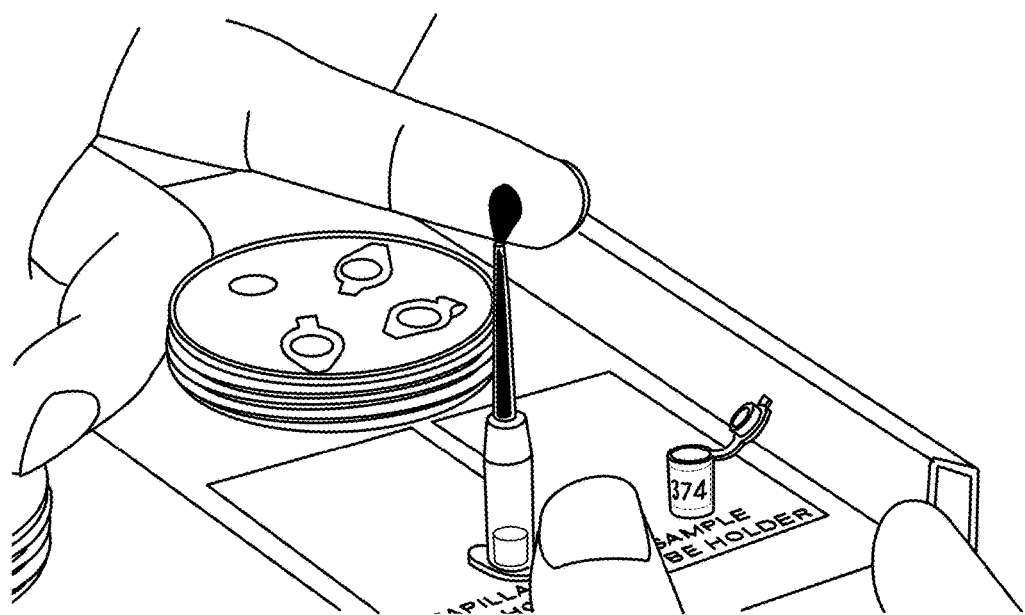
Figure 2H:
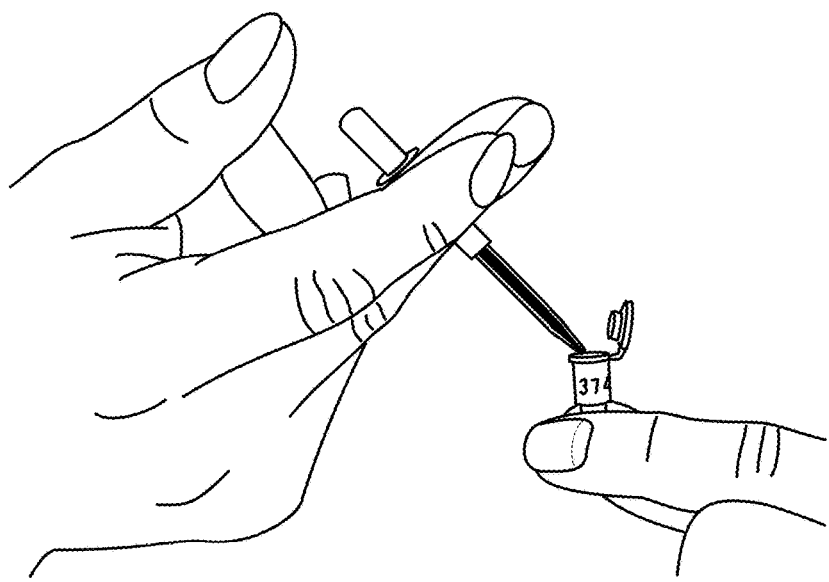
Figure 2I:
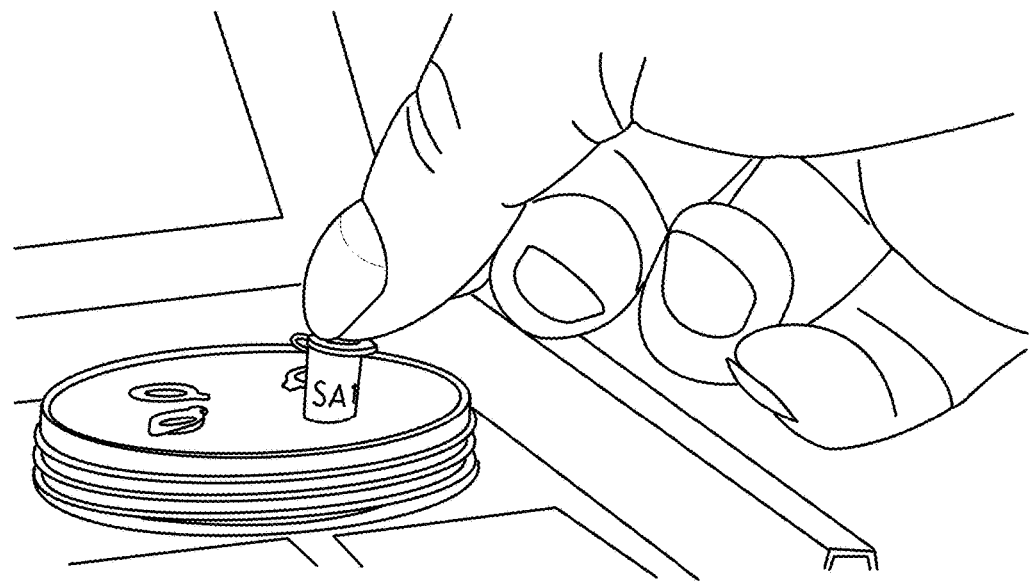
Figure 2J:
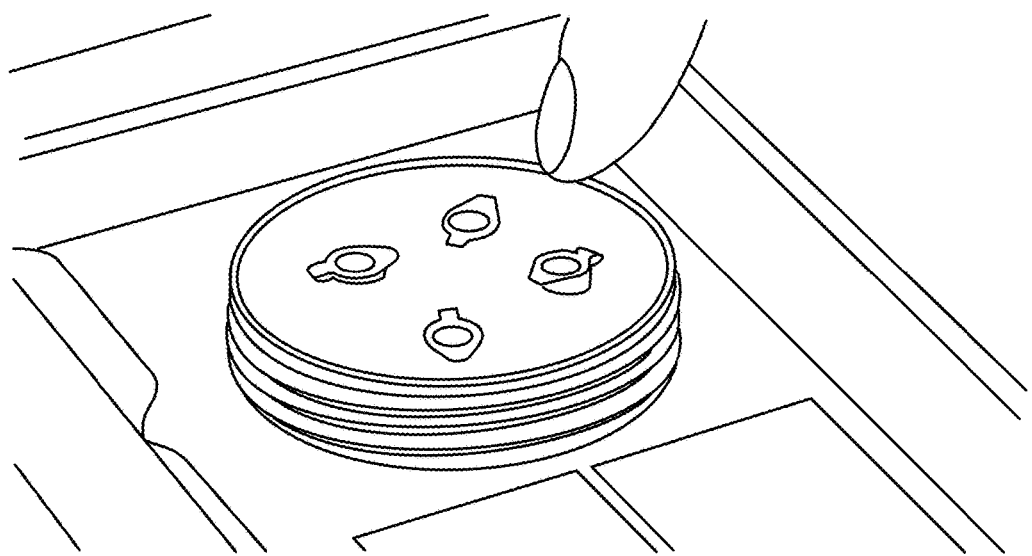
Figure 2K:
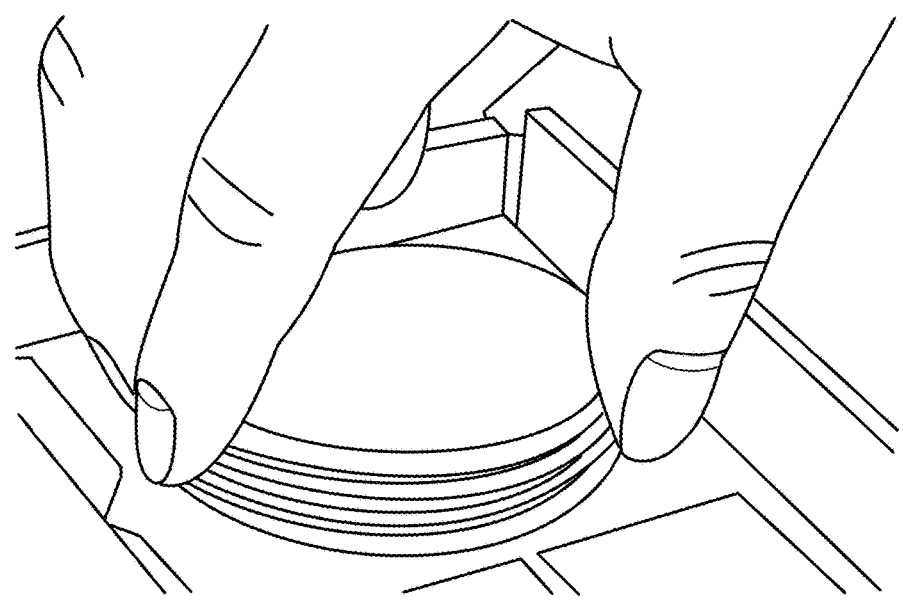

FIGS. 2A-2K shows components of an illustrative, but non-limiting embodiment of a home collection kit for the collection of blood samples for DNA damage evaluation and the use of that kit. FIG. 1A shows the sterile swab 108, drying pad 102, and disposable finger pricing lancet device 112 that might be found in a single packet 116. In one illustrative, but non-limiting mode of operation, a sample tube 118 is placed in a sample tube holder and a capillary blood collection device 114 is placed into a capillary tube holder with the inlet pointing up, e.g., as shown in FIGS. 2B and 2C. The site to be pricked (e.g., finger side or finger pad, or alternative site such a forearm, thigh above the knee, the heel (e.g., using heel lancet), and the like) is cleaned, e.g. using the sterile swab 108, and dried, e.g., using the drying pad 102. The site is then pricked using the sterile lancet device 112, e.g., as shown in FIG. 2D, and the finger may be optionally squeezed to produce a drop of blood as shown in FIG. 2E. The drop of blood is touched to the capillary blood collection device 114 whereby blood is drawn into the device by capillary action (FIG. 2F). This can be repeated until the collection device is full, e.g. until the blood reaches a mark indicating sufficient sample (see, e.g., FIG. 2G). Once full, the collection device 114 is used to transfer the blood into the sample tube 118 (see, e.g., FIG. 2H). This can be readily accomplished, for example, by operating the expulsion means (e.g., a plunger) to deliver the blood into the sample tube. After blood delivery, the sample tube is closed and typically agitated (e.g., for 10 to 300 seconds, more typically for 30 seconds to 1 minute, and in certain embodiment for about 30 seconds) to mix the blood with the solution (e.g. fixative) in the sample tube. The sample tube 118 can then be placed into the sample tube holder 120 (see, e.g., FIGS. 2I, 2J, and 2K) for storage and/or shipping. If the sample is to be stored, it is typically refrigerated.

It will be appreciated that the foregoing kit and methods of use are intended to be illustrative and non-limiting. Using the teaching provided herein other kit components can be added or various illustrated kit components can be substituted with equivalent.

EXAMPLES

The following examples are offered to illustrate, but not to limit the claimed invention.

Example 1

Fix Blood Samples for Shipping and Later Analysis.

Shipping conditions and fixative formula are important for this process. In certain embodiments a fixative reagent effective for stabilizing DNA damage during storage and shipping can be obtained by mixing paraformaldehyde, 1×PBS and EDTA so that the final concentrations are: about 1% to about 4% paraformaldehyde and about 10 mM to about 100 mM EDTA, and in certain embodiments, about 2% paraformaldehyde and about 50 mM EDTA. Fixative and whole blood are then mixed in a 1:1 ratio, leading to a mix of PBS and blood with a final concentration of 1% Paraformaldehyde and 25 mM EDTA. Our testing has shown that we can process blood keeping it for various periods of time after collection (e.g., up to about 14 days at 4° C. and up to about 5 days at room temperature) without a change in the measured number/amount of DNA damage per sample.

Sample Processing and Analysis

In typical embodiments, DNA damage is scored in specific white cell types. It was discovered that some white cells do not show any DNA damage and that individual blood samples can have broadly variable ratios of different white cell types. By measuring DNA damage in all white cells, damage levels can be incorrectly skewed based on cell populations in a sample. The way one presses on his/her finger or the duration of keeping a sample in the fixative can change white cell ratios and thus average DNA damage levels. By focusing on two specific cell types, this error can be eliminated.

The process of extracting white cells from fixed whole blood was developed from commercial reagents. Starting with EASYSEP™ Human T Cell Enrichment Kit kits sold by Stem Cell Technologies, protocols were modified and developed to isolate leukocytes from 50 µl of fixed blood instead of 1 ml of viable whole blood.

"Stem Cell" technology utilizes magnetic nanoparticles with antibodies to recognize specific white cell types. Once attached to the cells of interest, magnetic beads are captured with a powerful magnet (provided by "Stem Cell") and the white cells of interest are selected for further processing.

One illustrative, but non-limiting protocol exploits magnetic cell capture to perform immunocytochemistry on cells in suspension. Briefly cells are kept at the bottom of a 96 well plate by the combination of a strong magnetic field and special glue (BD CELL-TACK™) at the bottom of the wells. This streamlines the staining process, shortens cell isolation times, and reduces overall DNA break scoring protocol times.

DNA Damage Analysis.

The collection kits described herein are designed to effectively stabilize blood samples so that they can be shipped to a remote location for DNA damage analysis. Typically this analysis will be provided by a clinical and/or specialty laboratory.

In certain embodiments, DNA damage is evaluated using automated analysis of cell-preps. In one illustrative, but non-limiting embodiment, wells containing cell-samples are first scanned at low magnification (e.g., 10×) to identify where cells are located. Automated nuclear segmentation using local thresholding followed by watershed for separating touching nuclei can be used to identify cells. In order to predict what areas will have the highest cell density at high magnification (40×), the 10× image can be split into 4×4 panels, leading to 16 subpanels, representing the regions of the 40× field matching the 10× field. For each of these subpanels, a cell density and motorized stage positions of microscope can be computed automatically via cubic spline interpolation and stored. Once a well has been fully scan with a low magnification (e.g., 10×) objective, subpanels are sorted from highest to lowest density. The corresponding stage positions are revisited in order at high magnification (40×) and a full Z-stack (1.0 µm step, 9 slices) is then acquired for each subpanel in all fluorescent channels (nuclei, DNA damage, cell specificity markers). This method of acquisition leads to a minimum number of Z-stack images for a maximum number of cells. In certain embodiments, one requirement for adequate statistics of DNA damage is to image at least 500 cells per well.

In various embodiments, image analysis can done in-house using image processing software libraries (e.g., diplib, vtk, itk, FIJI, and the like). Certain methods are described in International PCT Publication WO 2013/187973, hereby incorporated by reference for the methods described therein. In certain embodiments, nuclear segmentation is done as described herein and spot detection is done immediately after acquisition via separate in-house software using wavelet algorithm published by Olivo-Marin (2002) *Pattern Recognition*, 35(9): 1989-1996, local thresholding and watershed separation. The imaging software creates large array of data collecting for each nucleus the following properties: 1) Size of nucleus; 2) Sphericity of nucleus (also called shape factor or P2A); 3) Intensity properties of nucleus (i.e. mean pixel intensity, total pixel intensity, max, min and standard deviation) in all channels being imaged; 4) Number of foci for each nucleus; 5) Mean, max, min, of foci in each nucleus; 6) Mean, max and min foci size for each nucleus; and 7) Probability of foci following a random spatial distribution in the nucleus. The same properties can also be computed for individual foci. The final result is the ability to reproducibly measure DNA damage levels with accuracy and precision as described in Neumaier et al. (2012) *Proc. Natl. Acad. Sci. USA*, 109(2): 443-448, hereby incorporated by reference for the methods and techniques described therein. It is noted that reproducibility is an important requirement for FDA approval.

In certain embodiments, multiple imaging features of specific samples described can be stored as feature vectors and can be correlated against individual personal information of the same sample: i.e. age, ethnicity, physical activity at moment of blood collection, and more generally life style and environmental conditions. A multilevel analysis approach can be used to identify which features are most responsive to age-related disease, genetic defects, cancer, and/or environmental factors. This large data platform for correlative analysis is showing that some cancers and aging correlate strongly with the average number of DNA damage foci per cell. Optimum combinations of features can be used as specific signature of the various lifestyles, genetic factors and personal information from the database.

Numerous methods exist to score DNA damage (see, e.g., PCT Publication No: PCT/US2013/031727 (WO 2013/187973 A1) which is incorporated herein for scoring methods described therein; Revel et al. (2003) *J. Appl. Toxicol.* 23(4): 255-161; Qiu et al. (2003) *Am. J. Pathol.* 162(6): 1961-1974; Saigusa et al. (2013) *J. Clin. Gastroenterol.* 47(9): e80-e866. doi: 10.1097/MCG.0b013e31828f51e1; and the like).

Once the DNA damage markers are scored, e.g., against a reference, the quantitative DNA damage data can be provided to the subject and in some embodiments, a corrective lifestyle change or regimen can be advocated or prescribed by a health professional based on the diagnosis information provided.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference in their entirety for all purposes.

What is claimed is:

1. A method for providing a service to provide a subject information regarding the state of a subject's DNA damage, said method comprising:
    a) receiving from a subject one or more sample tube(s) containing the subject's blood fixed in said tubes, wherein said collection tubes are from a home collection kit, where said kit comprises a package containing:
        a sterile lancet;
        a capillary blood collection device coated with an anti-coagulant to avoid coagulation of blood drawn into said capillary; and
        said one or more sample tubes, where each of said tubes contains a fixative, an anti-coagulant, and a buffer that provide fixation conditions such that blood loaded into said tubes can be shipped and/or stored without substantial changes in DNA break markers;
    b) isolating T, B and/or NK cells from said blood sample by
        i. conducting hypotonic lysis of erythrocytes (red blood cells) in fixed blood samples;
        ii. capturing of T, B, and/or NK cells from said sample using CD-specific antibodies;
        iii. coupling the antibody captured fixed T, B and/or NK cells to magnetic beads or nanoparticles;
        iv. exposing the antibody captured fixed T, B and/or NK cells coupled to magnetic beads or nanoparticles tubes to a strong magnetic field to immobilize the cells; and
        v. washing away unwanted cells and serum components leaving target cells of interest;
    c) affixing the isolated cells to the surface by an adhesive;
    d) labeling affixed cells with primary antibodies recognizing DNA damage markers and with secondary antibodies that are covalently conjugated to fluorescent chromophores to provide labeled cells; and
    e) imaging said labeled cells and scoring for DNA breaks in the cells.

2. A method for providing a service to provide a subject with information regarding the state of a subject's DNA damage comprising:
  a) receiving from a subject one or more sample tube(s) containing the subject's blood fixed in said tubes, wherein said collection tubes are from a home collection kit, where said kit comprises a package containing:
    a sterile lancet;
    a capillary blood collection device coated with an anti-coagulant to avoid coagulation of blood drawn into said capillary; and
    said one or more sample tubes, where each of said tubes contains a fixative, an anti-coagulant, and a buffer that provide fixation conditions such that blood loaded into said tubes can be shipped and/or stored without substantial changes in DNA break markers;
  b) isolating and/or identifying specific cell types for DNA damage scoring of cell type-specific DNA damage measurements from said blood sample by:
    i. conducting a cell type in fixed blood samples;
    ii. capturing of said cells from said sample using cell type-specific antibodies;
    iii. coupling the antibody captured cells to magnetic beads or nanoparticles;
    iv. exposing the antibody captured fixed cells coupled to magnetic beads or nanoparticles tubes to a strong magnetic field to immobilize the cells; and
    v. washing away unwanted cells and serum components leaving target cells of interest;
  c) affixing the isolated cells to the surface by an adhesive;
  d) labeling affixed cells with primary antibodies recognizing DNA damage markers and with secondary antibodies that are covalently conjugated to fluorescent chromophores; and
  e) imaging said labeled cells and score for DNA breaks in the cells.

3. The method according to any one of claim 1 or 2, wherein said capillary blood collection device is configured to collect about 10 µl to about 200 µl, or about 10 µl to about 100 µl of blood.

4. The method according to any one of claim 1 or 2, wherein said anticoagulant in said capillary blood collection device and in said sample tubes comprises EDTA or heparin.

5. The method according to any one of claim 1 or 2, wherein said fixative is selected from the group consisting of paraformaldehyde, methanol, ethanol, acetone, and urea.

6. The method according to any one of claim 1 or 2, wherein said fixative comprises paraformaldehyde.

7. The method of claim 6, wherein said fixative comprises about 0.1 percent up to about 10% paraformaldehyde.

8. The method of claim 7, wherein said anticoagulant in said sample tubes comprises EDTA and wherein said fixative, when mixed with blood leads to a mix of fixative and blood with a final concentration of 1% paraformaldehyde and 25 mM EDTA.

9. The method of claim 7, wherein the sample tubes contain about 2% paraformaldehyde and 50 mM EDTA in PBS, and the volume of fixative provided in the sample tube(s) is such that fixative and whole blood are mixed in a 1:1 ratio when the capillary collection device is dispensed into the sample-tube(s).

10. The method of claim 8, wherein:
  said anticoagulant in said sample tubes comprises about 10 mM up to about 100 mM EDTA; and
  said buffer in said sample tubes comprises phosphate buffered saline at about pH 7 to about pH 8.

* * * * *